United States Patent [19]

Upadek et al.

[11] 4,351,772
[45] Sep. 28, 1982

[54] 6(9)-ISOPROPYL-9(6)-METHYL-6,9-ETHANO-2-OXASPIRO[4,5]DEC-7-ENES

[75] Inventors: Horst Upadek, Erkrath; Klaus Bruns, Krefeld-Traar, both of Fed. Rep. of Germany

[73] Assignee: Henkel Kommanditgesellschaft auf Aktien, Düsseldorf-Holthausen, Fed. Rep. of Germany

[21] Appl. No.: 323,430

[22] Filed: Nov. 20, 1981

[30] Foreign Application Priority Data
Dec. 6, 1980 [DE] Fed. Rep. of Germany ....... 3046068

[51] Int. Cl.³ .......................................... C07D 307/94
[52] U.S. Cl. .................................. 549/331; 252/522 R
[58] Field of Search .................................... 260/346.11

[56] References Cited
U.S. PATENT DOCUMENTS
4,179,448  12/1979  Schulte-Elte et al. .......... 260/346.11

FOREIGN PATENT DOCUMENTS
2504618  8/1975  Fed. Rep. of Germany .
2527102  1/1976  Fed. Rep. of Germany .

Primary Examiner—Richard Raymond
Attorney, Agent, or Firm—Hammond & Littell, Weissenberger and Muserlian

[57] ABSTRACT

This invention is directed to terpene derivatives. More particularly, this invention relates to a mixture of isomers of the formula

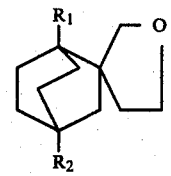

wherein $R_1$ and $R_2$, which are different from each other, are each methyl or isopropyl, the preparation thereof, and perfume compositions containing them.

1 Claim, No Drawings

6(9)-ISOPROPYL-9(6)-METHYL-6,9-ETHANO-2-OXASPIRO[4,5]DEC-7-ENES

FIELD OF THE INVENTION

This invention is directed to terpene derivatives. More particularly, this invention relates to terpene derivatives, the preparation thereof, and perfume compositions containing them.

BACKGROUND OF THE INVENTION

Because of the irregular availability of many natural fragrance components and the necessary adjustment to the changing tastes in fashion trends, the perfume industry has a steady demand for new fragrances that constitute valuable perfumes with interesting fragrance notes, either singly, that is, as perfuming agents, or in the form of perfume compositions. The specific synthesis of fragrances with desired olfactory qualities is impossible due to the little-known and unpredictable interrelationship between structure and fragrance characteristics. Therefore, it is a problem to find appropriate compounds that possess valuable fragrance characteristics.

OBJECTS OF THE INVENTION

It is an object of this invention to provide perfuming agents and perfume compositions having characteristic fragrances and excellent adherence.

It is also an object of this invention to provide perfuming agents and perfume compositions comprising mixtures of 6(9)-isopropyl-9(6)-methyl-6,9-ethano-2-oxaspiro[4,5]dec-7-ene isomers.

It is a further object of this invention to provide mixtures of 6(9)-isopropyl-9(6)-methyl-6,9-ethano-2-oxaspiro[4,5]dec-7-ene.

These and other objects of the invention will become more apparent in the discussion below.

DETAILED DESCRIPTION OF THE INVENTION

It has been found that a mixture of terpene derivatives comprising 6(9)-isopropyl-9(6)-methyl-6,9-ethano-2-oxaspiro[4,5]dec-7-ene isomers of the general formula

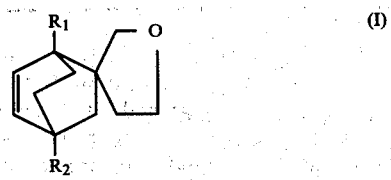

wherein $R_1$ and $R_2$, which are different from one another, are each methyl or isopropyl, possesses an animal-woody odor reminiscent of tobacco leaf and consequently represents a valuable new perfume agent which can advantageously be used as a perfuming agent in compositions for perfuming technical and cosmetic preparations. Useful perfume compositions comprise from about 1 to 50 percent by weight, based on the total weight of the perfume compositions, of the mixture of 6(9)-isopropyl-9(6)-methyl-6,9-ethano-2-oxaspiro[4,5]-dec-7-ene isomers.

The terpene derivatives of Formula I have not been previously known. The preparation of these derivatives in the form of a mixture of the structural isomers and stereoisomers is carried out by known syntheses of organic chemistry, which represent a novel preparation procedure in connection with the compounds of Formula I. Furthermore, reaction conditions have been determined that allow the preparation of the compounds according to the invention in especially good yields and with the purity required for a fragrance.

The starting materials for the synthesis are α-terpinene (II) and itaconic acid anhydride (III). These are converted into adduct (IV) by a Diels-Alder addition reaction. A mixture of the two structural isomers (IVa) and (IVb) is formed by this reaction. The Diels-Alder reaction can be especially advantageously carried out without solvents and with the use of a from about 10 to 20% molar excess of α-terpinene (II), based upon the itaconic acid anyhydride (III), at a temperature of from about 140° to 195° C. By reduction of the Diels-Alder adduct (IV) with a complex metallic hydride, 1(4)-isopropyl-4(1)-methyl-2-hydroxyethyl-2-hydroxymethyl-bicyclo[2,2,2]oct-5-ene is obtained, which in turn is composed of the structural isomers (Va) and (Vb). Complete reduction does not occur with the use of a reducing agent such as sodium borohydrate in isopropanol. The reduction is easier, that is, proceeds more easily to completion, when a reducing agent such as sodium bis(2-methoxyethoxy)-aluminium dihydride, which is easy to handle and is commercially available as 78% solution in toluene under the name Vitride ® from Hexcel Speciality Chemicals, is used as the complex metallic hydride. Even with a small, approximately 10%, molar excess of the reducing agent, a practically complete reduction of the adduct (IV) to the diol (V) is achieved. The diols (V) are converted, with the loss of water, into the cyclic ethers of the 6(9)-isopropyl-9(6)-methyl-6,9-ethano-2-oxaspiro[4,5]dec-7-enes of Formula I, without isolation from the reaction mixture, by the addition of an acid catalyst, for example, para-toluenesulfonic acid. In addition to the two structural isomer compounds (Ia) and (Ib), the two diastereomers possible with respect to the spiro-center 5 are formed in this synthesis.

The preparation procedure can be summarized by the following reaction scheme:

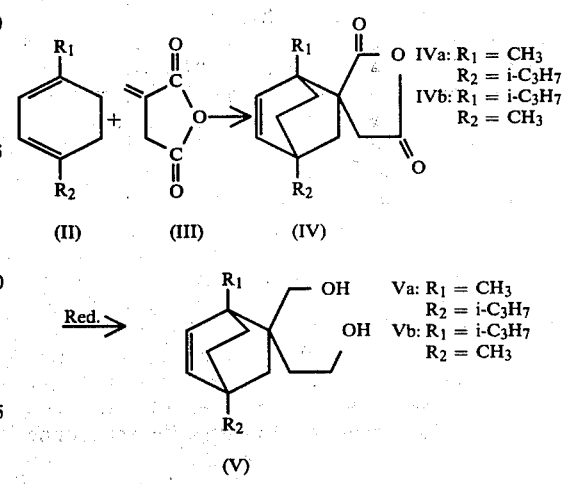

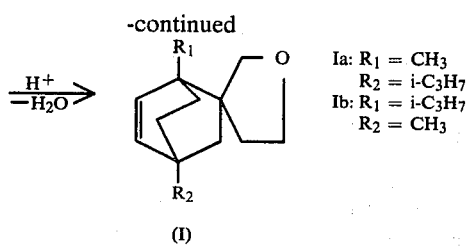

Ia: $R_1 = CH_3$
$R_2 = i\text{-}C_3H_7$
Ib: $R_1 = i\text{-}C_3H_7$
$R_2 = CH_3$ One advantage of the isomer mixture of the 6(9)-isopropyl-9(6)-methyl-6,9-ethano-2-oxaspiro[4,5]dec-7-ene is that it is characterized by an animal-woody odor reminiscent of tobacco leaf that has good staying quality or adherence, that is, it is lasting fragrance. Another advantage is that the new perfuming agent can be readily combined to form novel perfume compositions to which it imparts an interesting woody fragrance nuance.

The mixture of isomers of Formula I can be mixed with other perfumes in various quantitative proportions to form new perfume compositions. In general the mixture of isomers of Formula I in the perfume composition will comprise from about 1 to 50 percent by weight, based on the total weight of the perfuming composition. The remainder of the composition is comprised of conventional perfumery constituents. Perfume compositions of this type can be used directly as a perfume in extract perfumery, or, alternatively, for perfuming cosmetics, such as creams, lotions, toilet waters, aerosols, shampoos, bath preparations, soaps, technical articles, such as detergents and softeners, and the like. For the perfuming of the various products, the perfume compositions are generally added to these products in concentrations of from about 0.05 to 2 percent by weight, preferably from about 0.1 to 1 percent by weight, based upon the weight of the finished product.

The following examples are intended to illustrate the invention and are not to be construed as limiting the invention thereto.

EXAMPLES

Example 1

Preparation of 6(9)-isopropyl-9(6)-methyl-6,9-ethoan-2-oxaspiro[4,5]-dec-7-ene in the Form of the Mixture of Structural Isomers and Stereoisomers (a) Preparation of the Diels-Alder adduct IV from α-terpinene and itaconic acid anhydride.

An amount of 490.5 gm (3.6 mols) of α-terpinene and 336.3 gm (3 mols) of itaconic acid anhydride were heated for four hours at 145° to 160° C. After removal of the excess α-terpinene by distillation, 538 gm of adduct (IV) were collected at 145°–156° C./1.5 mbar.

(b) Reduction of the Diels-Alder adduct (IV) and ring formation to obtain 6(9)-isopropyl-9(6)-methyl-6,9-ethano-2-oxaspiro[4,5]dec-7-ene (I).

A quantity of 61.6 milliliters (0.22 mol) of Vitride ® were added dropwise within 45 minutes at 25° to 35° C. reaction temperature with ice cooling and under a nitrogen atmosphere to 24.8 gm (0.1 mol) of the adduct (IV) from step (a) in 67 ml of toluene. The reaction mixture was refluxed with agitation for two more hours, and the cooled, clear reaction solution was reacted slowly with 420 ml of 6 N hydrochloric acid with sufficient cooling that the temperature did not exceed 50° C. Agitation was continued until all solid components were dissolved, and the toluene phase was separated and washed once with water. The organic phase contained approximately 18 gm of diol (V) and was used directly for the subsequent dehydration. After the addition of 1.8 gm of p-toluene sulfonic acid to the toluene phase, the water was removed completely by refluxing. The cooled solution was neutralized with dilute sodium hydroxide solution, washed once with water, evaporated, and distilled. A total of 11.9 gm of 6(9)-isopropyl-9(6)-methyl-6,9-ethano-2-oxaspiro[4,5]dec-7-ene (I) was isolated at 73°–82° C./0.1 mbar.

$n_D^{20} = 1.5034$

IR (film): a.o. 3035 (=CH); 1372 and 1390 (isopropyl); 698 (cis-RCH=CHR′) cm$^{-1}$.

$^1$H-NMR (CDCl$_3$): =5.87–6.21 (m, 2H, olefinic H), 3.32–4.05 (m, 4H, —CH$_2$—O—), 0.75–2.30 (m, 18H).

Fragrance: animal-woody, reminiscent of tobacco leaf.

The following represents an example of a perfume composition according to the invention:

Example 2

Flowery, Woody Complex for Foaming Bath Formation

| Component | Parts by Weight |
|---|---|
| 6(9)-isopropyl-9(6)-methyl-6,9-ethano-2-oxaspiro-[4,5]dec-7-ene | 110 |
| Cyclamber ®, (13-Oxabicyclo-(10.3.0)-pentadecan), available from Henkel KGaA | 70 |
| Phenylethyl alcohol | 200 |
| Citronellol | 120 |
| Linalyl acetate | 75 |
| α-Isomethyl ionone | 70 |
| α-Hexylcinnamaldehyde | 60 |
| Ylang-ylang oil, synthetic | 60 |
| Benzylacetate | 50 |
| Cyclopentadecanolide, 10% in diethylphthalate | 40 |
| Methyldihydrojasmonate | 40 |
| Amyl salicylate | 30 |
| Vetivenol | 30 |
| Oil of neroli, synthetic | 20 |
| Heliotropin | 15 |
| Leaf alcohol, 10% in diethylphthalate | 10 |
| | 1000 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A mixture of isomers of the formula

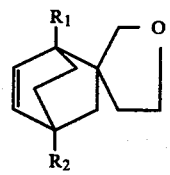

wherein R$_1$ and R$_2$, which are different from each other, are each methyl or isopropyl.

* * * * *